United States Patent [19]

Yamada et al.

[11] Patent Number: 5,753,472
[45] Date of Patent: May 19, 1998

[54] DNA FRAGMENT ENCODING A POLYPEPTIDE HAVING NITRILE HYDRATASE ACTIVITY, A TRANSFORMANT CONTAINING THE GENE AND A PROCESS FOR THE PRODUCTION OF AMIDES USING THE TRANSFORMANT

[75] Inventors: Hideaki Yamada; Toru Nagasawa, both of Kyoto; Teruhiko Beppu, Tokyo; Sueharu Horinouch, Tokyo; Makoto Nishiyama, Tokyo, all of Japan

[73] Assignee: Nitto Chemical Industry Co. Ltd., Japan

[21] Appl. No.: 461,836

[22] Filed: Jun. 5, 1995

Related U.S. Application Data

[63] Continuation of Ser. No. 28,463, Mar. 9, 1993, which is a continuation of Ser. No. 694,747, May 2, 1991, abandoned.

[51] Int. Cl.$^6$ .................. C12P 13/02; C12N 1/00; C12N 1/21; C12N 5/10; C12N 15/55; C12N 15/63; C12N 91/78
[52] U.S. Cl. .................. 435/129; 435/227; 435/252.3; 435/252.33; 435/254.11; 435/325; 435/410; 435/320.1; 435/874; 536/23.2
[58] Field of Search ............... 435/227, 252.33, 435/240.1, 320.1, 874, 23.2, 252.3, 254.11, 325, 410, 129; 536/69.1, 23.2

[56] References Cited

U.S. PATENT DOCUMENTS

| 4,001,081 | 1/1977 | Commeyras et al. | 435/129 |
|---|---|---|---|
| 4,248,968 | 2/1981 | Watanabe et al. | 435/129 |
| 4,637,982 | 1/1987 | Yamada et al. | 435/129 |

FOREIGN PATENT DOCUMENTS

| 0188316 | 7/1986 | European Pat. Off. |
|---|---|---|
| 307926 | 3/1989 | European Pat. Off. |
| 362829A2 | 4/1990 | European Pat. Off. |
| 2633938A | 11/1990 | France |
| 2119778 | 5/1990 | Japan |

OTHER PUBLICATIONS

Ikehata et al., 1989, Eur. J. Biochem. 181(3): 563–570.
Nagasawa et al., 1987, Eur. J. Biochim. 162:691–698.
Asano et al., 1982, Agric. Biol. Chem. 46(5):1183–1189.
Yamada, 1986, Agric. Biol. Chem. 50(1):2859–2865.
Nishiyama et al., 1991, J. Bacteriol. (Apr. 1991) 173(8): 2465–72.
Abstract entitled "2Xa3 Cloning and Structure Analysis of a Nitrilhydratase (NHase) Gene of *Pseudomonas chlororaphis* B23" by Nishida et al., 1990 (Mar. 1990) 64(03) Nippon Nogeikagaku Kaishi and Applicants' translation thereof.
Abstract entitled "2Xp3 Cloning of Two Types of Nitrihydratase (NHase) Genes Derived from *Rhodococcus rhodochrous*" by Kobayashi et al., 1990, (Mar., 1990) 64(03) Nippon Nogeikagaku Kaishi and Applicants' translation thereof.
Ikehata et al., Oct. 10, 1988, Lecture Summary, Japan Soc. for Fermentation, 22 (130), 1988 and Applicants translation thereof.
Abstract entitled "2Xo2 Cloning of the Amidase Gene of *Rhodococcus* sp. N–774 and Expression of the Gene in *E. coli*" by Hashimato et al., 1990 (Mar., 1990) 64(03) Nippon Nogeikagaku Kaishi and Applicants' translation thereof.
Nagasawa et al., Jul., 1990, Yuki Gosei Kagaku Kyoskaishi 48(11): 1072–73.
Hjort et al., 1990, (Mar. 20, 1990) J. Chem. Technol. 48(11): 217–226.
Yamada et al., 1990, Ann. NY. Acad. Sci., Dec. 28, 1990, 613: 142–154.
Mayaux et al., 1990, J. Bacteriol., Dec., 1990, 172(12): 6764–73.
Sun et al., 1990, Gongye Weishengwu, 1990 20(3): 18–20.
Hashimoto et al., 1991, Biochim. Biophys Acta 1088(2): 225–233.
Nagasawa et al., 1988, Biochim. Biophys. Res. Commun. 155(2): 1008–1016.
Abstract entitled Purification and Characterization of Nitrile Hydratase Produced by *Rhodococcus rhodochrous* J. Nagasawa et al., 1988, Seikagaku vol. 60(8), p. 647, 1988, and Applicants' translation thereof.

*Primary Examiner*—Keith C. Furman
*Assistant Examiner*—Gabriele Bugaisky
*Attorney, Agent, or Firm*—Pennie & Edmonds

[57] ABSTRACT

The present invention has disclosed the amino acid sequence and nucleotide sequence of the α- and β-subunits of two types of nitrile hydratase derived from *Rhodococcus rhodochrous* J-1. The DNA fragment encoding nitrile hydratase is inserted into an expression vector and the recombinant vector is used for transformation. The transformant contains multiple copies of the gene and can produce much higher level of nitrile hydratase compared with conventionally used microorganisms.

14 Claims, 1 Drawing Sheet

1

DNA FRAGMENT ENCODING A POLYPEPTIDE HAVING NITRILE HYDRATASE ACTIVITY, A TRANSFORMANT CONTAINING THE GENE AND A PROCESS FOR THE PRODUCTION OF AMIDES USING THE TRANSFORMANT

This is a continuation of application Ser. No. 08/028,463, filed Mar. 9, 1993; which in turn is a continuation of application Ser. No. 07/694,747 filed on May 2, 1991, now abandoned.

FIELD OF THE INVENTION

The present invention relates to a DNA fragment derived from *Rhodococcus rhodochrous* J-1 and encoding a polypeptide having nitrile hydratase activity which hydrates nitriles to amides. The invention also relates to a recombinant DNA containing the above DNA fragment, and a transformant transformed with the recombinant DNA. The present invention further relates to a method of producing nitrile hydratase using the transformant and of amides using nitrile hydratase.

PRIOR ART

Nitrile hydratase or nitrilase is known as an enzyme that hydrates nitriles to amides. Microorganisms that produce nitrile hydratase include those belonging to the genus Bacillus, the genus Bacteridium, the genus Micrococcus and the genus Brevibacterium (See, JP-B-62-21517/1989, U.S. Pat. No. 4,001,081), the genus Corynebacterium and the genus Nocardia (See, JP-B-56-17918/1981, U.S. Pat. No. 4,248,968), the genus Pseudomonas (See, JP-B-59-37951/1984, U.S. Pat. No. 4,637,982), the genus Rhodococcus, the genus Arthrobacter and the genus Microbacterium (See, JP-A-61-162193/1986, EP-A-0188316), and *Rhodococcus rhodochrous* (See, JP-A-2-470/1990, EP-A-0307926).

Nitrile hydratase has been used to hydrate nitriles to amides. In the invention, microorganisms are engineered to contain multiple copies of a recombinant DNA encoding nitrile hydratase according to a recombinant DNA technology. The recombinant produces a remarkably high level of nitrile hydratase compared with conventionally used microorganisms.

The present inventors previously disclosed a DNA fragment derived from *Rhodococcus* sp. N-774 (FERM BP-1936) which also encodes a polypeptide having nitrile hydratase activity (JP-A-2-119778/1988).

In-contrast, the present inventors utilizes a DNA fragment derived from *Rhodococcus rhodochrous* J-1 for the production of nitrile hydratase. We isolated the gene encoding nitrile hydratase, inserted the gene into a suitable plasmid vector and transformed an appropriate host with the recombinant plasmid, thus successfully obtained the transformant producing nitrile hydratase which has high activity also on aromatic nitriles.

SUMMARY OF THE INVENTION

The present invention relates to
(1) a DNA$^{(H)}$ fragment encoding a polypeptide having nitrile hydratase activity, said polypeptide comprising $\alpha^{(H)}$-subunit as defined in the Sequence Listing by SEQ ID: No. 1 and $\beta^{(H)}$-subunit as defined in the Sequence Listing by SEQ ID; No. 2.
(2) A DNA$^{(L)}$ fragment encoding a polypeptide having nitrile hydratase activity, said polypeptide comprising $\alpha^{(L)}$-subunit as defined in the Sequence Listing by SEQ ID: No. 3 and $\beta^{(L)}$-subunit as defined in the Sequence Listing by SEQ ID: No. 4.
(3) the DNA$^{(H)}$ fragment of (1) which contains a nucleotide sequence encoding said $\alpha^{(H)}$- and $\beta^{(H)}$-subunits, comprising: DNA sequence of $\alpha^{(H)}$-subunit as defined in the Sequence Listing by SEQ ID: No. 5 and DNA sequence of $\beta^{(H)}$-subunit as defined in the Sequence Listing by SEQ ID: No. 6.
(4) the DNA$^{(L)}$ fragment of (2) which contains a nucleotide sequence encoding said $\alpha^{(L)}$- and $\beta^{(L)}$-subunits, comprising: DNA sequence of $\alpha^{(L)}$-subunit as defined in the Sequence Listing by SEQ ID: No. 7 and DNA sequence of $\beta^{(L)}$-subunit as defined in the Sequence Listing by SEQ ID: No. 8.
(5) a recombinant DNA comprising the DNA$^{(H)}$ or the DNA$^{(L)}$ of (1)–(4) in a vector; and
(6) a transformant transformed with the recombinant DNA of (5).
(7) a method for the production of nitrile hydratase which comprises culturing the transformant as described in (6) and recovering nitrile hydratase from the culture;
(8) a method for the production of amides which comprises hydrating nitriles using nitrile hydratase as described in (7) to form amides; and
(9) a method for the production of amides which comprises culturing the transformant as described in (6), and hydrating nitriles using the resultant culture, isolated bacterial cells, treated matter thereof, or a fixed material of them, to form amides.

The present invention is described in detail as follows.

The present invention is carried out by the steps (1)–(8):

(1) Isolation and Purification of Nitrile Hydratase and Partial Amino Acid Sequencing of Nitrile Hydratase Two types of nitrile hydratase (designated as H type and L type, respectively) are isolated and purified from *Rhodococcus rhodochrous* J-1 (FERM BP-1478) and the both enzymes are separated into $\alpha$ and $\beta$ subunits using HPLC. N-Terminal amino acid sequence each of the subunits is determined and shown in the Sequence Listing by SEQ ID: Nos. 9–12.

(2) Preparation of a DNA Probe for a Nitrile Hydratase Gene

A DNA probe is prepared from JM105/pYUK121 (FERM BP-1937) as described in JP-A-2-119778/1990 due to the high degree of homology in the amino acid sequence between the nitrile hydratase $\beta$ subunit of *Rhodococcus* sp. N-774 described in said Japanese Patent Official Gazette and those of *Rhodococcus rhodochrous* J-1. Plasmid pYUK121 containing nitrile hydratase gene derived from *Rhodococcus* sp. N-774 is prepared from a JM105/pYUK121 culture. pYUK121 DNA is digested with SphI and SalI. The SphI-SalI fragment contains the nitrile hydratase gene (shown in the Sequence Listing by SEQ ID: No. 13) of *Rhodococcus* sp. N-774. The DNA fragment is radiolabeled.

(3) Detection of a DNA Segment Containing a Nitrile Hydratase Gene from the Chromosome of *Rhodococcus rhodochrous* J-1

Chromosomal DNA is prepared from a *Rhodococcus rhodochrous* J-1 culture. The chromosomal DNA is digested with restriction enzymes and hybridized to the probe described in (2) using a Southern hybridization method [Southern, E. M., J. Mol. Biol. 98, 503 (1975)].

Two DNA fragments of a different length are screened.

(4) Construction of a Recombinant Plasmid

A recombinant plasmid is constructed by inserting the chromosomal DNA fragment as prepared in (3) into a plasmid vector.

(5) Transformation and Screening of the Transformant Containing the Recombinant Plasmid Transformants are prepared using the recombinant plasmid as described in (4). The transformant containing the recombinant plasmid is selected using the probe as described in (2) according to a colony hybridization method [R. Bruce Wallace et. al., Nuc. Aci. Res. 9, 879 (1981)]. Additionally, the presence of the nitrile hydratase gene in the recombinant plasmid is confirmed using a Southern hybridization method. The plasmids thus selected are designated as pNHJ10H and pNHJ20L.

(6) Isolation and Purification of Plasmid DNA and Construction of the Restriction Map Plasmid DNAs of pNHJ10H and pNHJ20L as prepared in (5) are isolated and purified. The restriction map of the DNAs is constructed (FIG. 1) to determine the region containing nitrile hydratase gene.

(7) DNA Sequencing

The extra segment of the inserted DNA fragment in pNHJ10H and pNHJ20L is excised using an appropriate restriction enzyme. The inserted DNA fragment is then used for sequencing. The nucleotide sequence of the DNA fragment (SEQ: ID Nos. 14, 15) reveals that it contains the sequence deduced from the amino acid sequence as described in (1).

(8) Production of Nitrile Hydratase Using the Transformant and Conversion of Nitriles to Amides The transformant as described in (8) is cultured. The bacterial cells are mixed with nitriles, a substrate of nitrile hydratase, and amides are produced.

Rhodococcus rhodochrous J-1 was deposited with Fermentation Research Institute, Agency of Industrial Science and Technology, and was assigned the accession number FERM BP-1478. A transformant TG1/pNHJ10H containing pNHJ10H as described in (5) and a transformant TG1/pNHJ20L containing pNHJ20L as described in (5) were deposited with the above and assigned the accession number FERM BP-2777 and FERM BP-2778, respectively.

Any vectors including a plasmid vector (e.g., pAT153, pMP9, pHC624, pKC7, etc.), a phage vector (e.g., λgt11 (Toyobo), Charon 4A (Amersham), etc.) may be used. Enzymes which may be used include SphI, SalI, EcoRI, BamHI, SacI and the like, which are commercially available (Takara Shuzo). Various hosts may be used for transformation including but not limited to E. coli JM105 and E. coli TG1.

Culture media for the transformant are those ordinarily used in the art.

Conversion of nitriles to amides is carried out using nitrile hydratase, crude nitrile hydratase, the culture of the transformant, the isolated bacterial cells or treated matter thereof, and the like, prepared from the culture of the transformant.

Suitable nitriles in the invention include aromatic nitriles having 4–10 carbon atoms in the aromatic moiety and aliphatic nitriles having 2–6 carbon atoms, which are described in the European Patent Publication No. 0,307,926. Typical examples of the nitriles are 4-, 3- and 2-cyanopyridines, benzonitrile, 2,6-difluorobenzonitrile, 2-thiophene carbonitrile, 2-furonitrile, cyanopyrazine, acrylonitrile, methacrylonitrile, crotonitrile, acetonitrile and 3-hydroxypropionitrile.

The Effect of the Invention

The present invention has disclosed the amino acid sequence and nucleotide sequence of the α- and β-subunits of two types of nitrile hydratase derived from Rhodococcus rhodochrous J-1. The DNA fragment encoding nitrile hydratase is inserted into an expression vector and the recombinant vector is used for transformation. The transformant contains multiple copies of the gene and can produce much higher level of nitrile hydratase compared with conventionally used microorganisms.

Figure 1A:
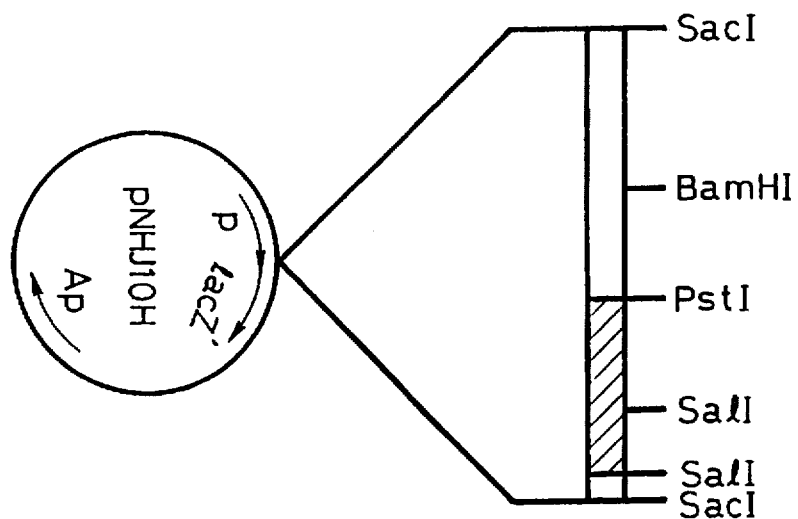
FIG. 1 shows restriction maps of recombinant plasmids, pNHJ10H and pNHJ20L.

The present invention will be illustrated in detail in the following Example which is not intended to limit the scope of the invention.

The following abbreviation is used in Example.

TE: Tris-HCl (10 mM; pH 7.8), EDTA (1 mM, pH 8.0)
TNE: Tris-HCl (50 mM; pH 8.0), EDTA (1 mM, pH 8.0), NaCl (50 mM)
STE: Tris-HCl (50 mM; pH 8.0), EDTA (5 mM, pH 8.0), Sucrose (35 mM)
2×YT medium: 1.6% Trypton; 1.0% Yeast extract, 0.5% NaCl

EXAMPLE (1) Isolation and Purification of Nitrile Hydratase and Partial Amino Acid Sequencing of Nitrile Hydratase Rhodococcus rhodochrous J-1 was cultured in a medium (3 g/l of yeast extract, 0.5 g/l of $KH_2PO_4$, 0.5 g/l of $K_2HPO_4$, 0.5 g/l of $MgSO_4.4H_2O$, 0.01 g/l of $CoCl_2$, and 3 g/l of crotonamide, pH 7.2) at 28° C. for 80 hours. The bacterial cells were harvested. 50 g of the bacterial cells was disrupted and fractionated with ammonium sulfate. The sample was dialyzed and the dialysate was centrifuged. The supernatant was loaded on DEAE-Cellulofine chromatography, Phenyl-Sepharose chromatography, Sephadex G-150 chromatography and Octyl-Sepharose chromatography. Two fractions with enzyme activity were obtained and dialyzed. The dialysates were loaded on a high performance liquid chromatography using a reversed phase column (Senshu Pak VP-304-1251, Senshu Kagaku), and two respective subunits (α and β) were obtained. N-terminal amino acid sequence of $\alpha_1^{(H)}$-, $\beta_1^{(H)}$-, $\alpha_1^{(L)}$- and $\beta_1^{(L)}$-subunits was determined using an Applied Biosystems model 470A protein sequencer. The amino acid sequences are shown in the Sequence Listing by SEQ ID: Nos. 9–12.

(2) Preparation of a DNA Probe for Nitrile Hydratase Gene

E. coli JM105 (FERM BP-1937) containing pYUK121 was cultured in 100 ml of 2×YT medium containing 50 μg/ml of ampicillin at 30° C. overnight (12 hours). The bacterial cells were harvested and TNE was added to the cells. The cell suspension was then centrifuged. 8 ml of STE and 10 mg of lysozyme were added to the pellet. The mixture was incubated at 0° C. for five minutes followed by the addition of 4 ml of 0.25M EDTA, 2 ml of 10% SDS and 5 ml of 5M NaCl were then added to the mixture at room temperature. The resultant mixture was incubated at 0°–40° C. for three hours and then ultracentrifuged. ½ volume of 30% PEG 6000 was added to the supernatant. The mixture was incubated at 0°–40° C. overnight (12 hours) and centrifuged. TNE was added to the pellet to bring the volume to 7.5 ml and CsCl was then added to the suspension. The mixture was centrifuged to remove proteins. Then, 300–500 mg/ml of ethidium bromide was added to the supernatant. The mixture was transferred to a centrifuge tube. The tube was heat-sealed and then ultracentrifuged. cccDNA was extracted using a peristaltic pump. A bit more than equal amount of isopropyl alcohol saturated with water was added to the extract to rid of ethidium bromide. The sample was dialyzed against TE. About 3 ml of purified pYUK121 was obtained.

pYUK121 DNA was digested with SphI and SalI, resulting in a 2.07 kb DNA fragment containing a nitrile hydratase gene derived from Rhodococcus sp. N-774. The fragment was radiolabeled with $^{32}P$ to produce a probe. The nucleotide sequence of the probe is shown in the Sequence Listing by SEQ ID: No. 13.

(3) Preparation of a DNA Fragment Containing a Nitrile Hydratase Gene of Chromosome

*Rhodococcus rhodochrous* J-1 was cultured in 100 ml of a medium (10 g/l of glucose, 0.5 g/l of $KH_2PO_4$, 0.5 g/l of $K_2HPO_4$, 0.5 g/l of $MgSO_4.7H_2O$, 1 g/l of yeast extract, 7.5 g/l of peptone, 0.01 g/l of $CoCl_2$, 7.5 g/l of urea, 1% glycine or 0.2 µg/ml of ampicillin, 1 l of water, pH 7.2). The bacterial cells were harvested and the pellet was washed with TNE. The pellet was then suspended in 10 ml of TE. 4 ml of 0.25M EDTA, 10–20 mg of lysozyme, 10–20 mg of achromoprotease and 10 ml of 10×SDS were added to the suspension. The suspension was incubated at 37° C. for three hours. 15 ml of phenol was added to the suspension. The mixture was incubated at room temperature for 15 minutes and then centrifuged. The upper layer was removed, and 0.7 ml of 2.5M sodium acetate and diethyl ether were added to the supernatant. The mixture was centrifuged and the upper layer was discarded. Two volumes of ethanol were added to the bottom layer and DNA was removed with a glass rod. DNA was rinsed for five minutes each with TE:ethanol 2:8, 1:9, and 0:10 (v/v). DNA was then resuspended in 2–4 ml of TE (37° C.). 10 µl of a mixture of RNase A and $T_1$ was added to the suspension and the mixture was incubated at 37° C. An equal amount of phenol was added to the mixture which was then centrifuged. More than equal amount of ether was added to the supernatant. The mixture was centrifuged again, and the upper layer was discarded and the bottom layer was saved. The bottom layer was dialyzed against 2 l of TE containing a small amount of chloroform overnight and further dialyzed against fresh TE for 3–4 hours. 4 ml of crude chromosomal DNA was obtained.

10 µl of TE, 3 µl of reaction buffer (10×) and 2 µl of SacI were added to 15 µl of crude chromosomal DNA. The mixture was incubated at 37° C. for an hour and electrophoresed on an agarose gel at 60 V for three hours. The Southern hybridization of chromosomal DNA was carried out using the probe as described in (2). About 6.0 kb and 9.4 kb fragments were found to show a strong hybridization.

15 µl of chromosomal DNA was digested with SacI and electrophoresed on an agarose gel, as described above. 6.0 kb and 9.4 kb DNA fragments were cut out from the gel and taken in three volumes each of 8M $NaClO_4$. After solubilization, each solution was dotted on GF/C (Whatman) filter paper (6 mm in diameter). Ten drops (≅100 µl) of TE containing 6M $NaClO_4$ and then ten drops (≅100 µl) of 95% ethanol were added to the filter paper. The paper was air-dried for 3 minutes and placed in 0.5 ml Eppendorf tube. 40 µl of TE was added to the tube and the whole was incubated at 47° C. for 30 minutes. The tube was then centrifuged. About 40 µl of the supernatant was obtained which contained 6.0 kb and 9.4 kb DNA fragments containing a nitrile hydratase gene of chromosomal DNA.

The method of inserting the 6.0 kb DNA fragment into a vector is described below. The same method is applied for the insertion of the 9.4 kb DNA fragment into a vector.

(4) Insertion of the Chromosomal DNA Fragment into a Vector

10 µl of TE, 3 µl of reaction buffer (10×) and 2 µl of SacI was added to 10 µl of pUC19. The mixture was incubated at 30° C. for an hour. 2 µl of 0.25M EDTA was added to the mixture to stop the reaction. Then, 7 µl of 1M Tris-HCl (pH 9) and 3 µl of BAP (bacterial alkaline phosphatase) were added to the mixture. The mixture was incubated at 65° C. for an hour. TE was then added to the mixture to make a total volume to 100 µl. The mixture was extracted 3× with an equal amount of phenol. An equal amount of ether was added to the extract. The bottom layer was removed and 10 µl of 3M sodium acetate and 250 µl of ethanol were added to the bottom layer. The mixture was incubated at −80° C. for 30 minutes, centrifuged, dried, and resuspended in TE.

5 µl of pUC19 DNA thus obtained and 40 µl of the 6.0 kb DNA fragment as described in (3) were mixed. 6 µl of ligation buffer, 6 µl of ATP (6 mg/ml) and 3 µl of T4 DNA ligase were added to the mixture. The mixture was incubated at 4° C. overnight (12 hours) to produce the recombinant plasmid containing the 6.0 kb DNA fragment encoding the desired enzyme in the SacI site of pUC19.

(5) Transformation and Screening of Transformants

*E. coli* TG1 (Amersham) was inoculated into 10 ml of 2×YT medium and incubated at 37° C. for 12 hours. After incubation, the resultant culture was added to fresh 2×YT medium to a concentration of 1%, and the mixture was incubated at 37° C. for two hours. The culture was centrifuged and the pellet was suspended in 5 ml of cold 50 mM $CaCl_2$. The suspension was placed on ice for 40 minutes and then centrifuged. 0.25 ml of cold 50 mM $CaCl_2$ and 60 µl of the recombinant DNA as described in (4) were added to the pellet. The mixture was incubated at 0° C. for 40 minutes, heat-shocked at 42° C. for two minutes, placed on ice for five minutes, and added to 10 ml of 2×YT medium. The mixture was incubated at 37° C. for 90 minutes with shaking, then centrifuged. The pellet was suspended in 1 ml of 2×YT medium, and two 10 µl aliquots of the suspension were plated on a 2×YT agar plate containing 50 µg/ml of ampicillin separately. The plate was incubated at 37° C. The colony grown on the plate was selected by the colony hybridization method: The colony was transferred to a nitrocellulose filter and digested. The DNA was fixed on the filter and hybridized to the probe as described in (2). The filter was autoradiographed and a recombinant colony was selected. Additionally, the presence of a nitrile hydratase gene in the transformant was confirmed according to the Southern hybridization method.

(6) Isolation and Purification of Recombinant Plasmid and Construction of the Restriction Map of the Inserted DNA Fragments The transformant selected as described in (5) was grown in 100 ml of 2×YT medium containing 50 µg/ml of ampicillin at 37° C. overnight (12 hours). The bacterial cells were harvested and TNE was added to the cells. The cells were collected again by centrifugation, and 8 ml of STE and 10 mg of lysozyme were added to the cells. The mixture was incubated at 0° C. for five minutes. 4 ml of 0.25M EDTA, 2 ml of 10% SDS (at room temperature) and 5 ml of 5M NaCl were added to the mixture. The mixture was incubated at 0°–46° C. for three hours, and ultracentrifuged. ½ volume of 30% PEG 6000 was added to the supernatant. The mixture was incubated at 0°–4° C. overnight (12 hours) and centrifuged again. TNE was added to the pellet to bring the volume up to 7.5 ml. CsCl was added to the suspension to rid of proteins. Then, 300–500 mg/ml of ethidium bromide was added to the supernatant and the mixture was transferred to a centrifuge tube. The tube was heat-sealed and ultracentrifuged. cccDNA was removed using a peristaltic pump. A bit more than equal amount of isopropyl alcohol saturated with water was added to cccDNA to remove ethidium bromide. The DNA sample was dialyzed against TE, resulting in about 3 ml of purified recombinant DNA. The recombinant plasmid thus obtained containing a 6.7 kb DNA fragment was designated as pNHJ10H (The recombinant plasmid containing a 9.4 kb DNA fragment was designated as pNHJ20L).

Figure 1B:
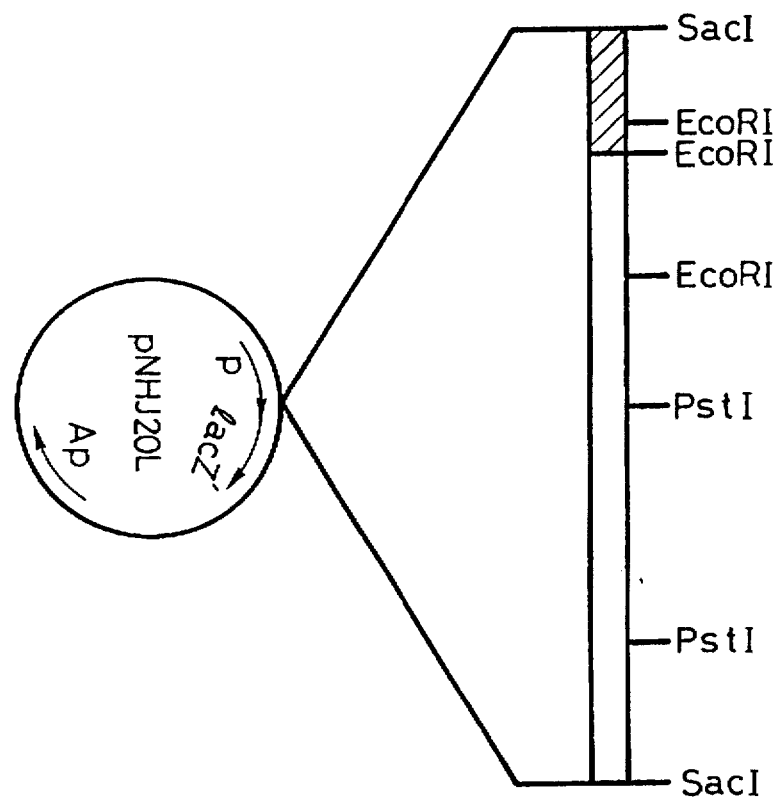

These plasmid DNAs were digested with EcoRI, BamHI, PstI, SacI and SalI. The restriction maps were constructed and are shown in FIG. 1.

(7) DNA Sequencing

The location of a nitrile hydratase gene in the DNA fragment of pNHJ10H was determined according to the restriction map constructed and to the Southern hybridization method. An extra segment in pNHJ10H was cleaved off with PstI and SalI; The 6.0 kb DNA fragment resulted in 1.97 kb. Similarly, an extra segment in pNHJ20L was cleaved off with EcoRI and SacI; The 9.4 kb DNA fragment resulted in 1.73 kb.

These DNA fragments were sequenced by the Sanger method [Sanger, F., Science 214: 1205–1210 (1981)] using M13 phage vector. The nucleotide sequence of the 1.97 kb DNA fragment (pNHJ10H) and the 1.73 kb DNA fragment (pNHJ20L) are shown in the Sequence Listing by SEQ ID: No. 14 and SEQ ID: No. 15, respectively.

The amino acid sequence deduced from the nucleotide sequence was found fully identical to the amino acid sequence as determined in (1). The sequence analysis also revealed that the DNA fragment contained the sequence coding for the α- and β-subunits.

(8) Production of Nitrile Hydratase Using the Transformant and Conversion of Nitriles to Amides Using Nitrile Hydratase TG1/pNHJ10H and TG1/pNHJ20L were inoculated into 10 ml of 2×YT medium containing 50 μg/ml of ampicillin and incubated at 30° C. overnight (12 hours). 1 ml of the resultant culture was added to 100 ml of 2×YT medium (50 μg/ml of ampicillin, 0.1 g of $CoCl_2.6H_2O/l$). The mixture was incubated at 30° C. for 4 hours. IPTG was added to the mixture to a final concentration of 1 mM. The mixture was incubated at 30° C. for 10 hours. After harvesting the cells, the cells were suspended in 5 ml of 0.1 M phosphate buffer (pH 7.5). The suspensions were disrupted by sonification for 5 min and centrifuged at 12,000 ×g for 30 min. The resulting supernatants were used for the enzyme assay. The enzyme assay was carried out in a reaction mixture (12 ml) containing 50 mM potassium phosphate buffer (pH 7.5), 6 mM benzonitrile and an appropriate amount of the enzyme. The reaction was carried out at 20° C. for 30 min and stopped by the addition of 0.2 ml 1M HCl. The amount of benzamide formed in the reaction mixture was determined by EPLC. As a control, the mixture obtained by the same procedure as described above but from E. coli TG1 was used. The levels of nitrile hydratase activity in cell-free extracts of E. coli containing pNHJ10H and pNHJ20L were $1.75×10^{-3}$ and $6.99×10^{-1}$ units/mg, respectively, when cultured in 2×YT medium in the presence of $CoCl_2$ and IPTG. Benzamide was found in the reaction mixture of TG1/pNHJ10H and pNHJ20L, whereas no benzamide was found in the reaction mixture of TG1. A number of references are cited herein, the disclosures of which are incorporated in their entirities, by reference herein.

What is claimed is:

1. An isolated DNA$^{(H)}$ fragment encoding a polypeptide having nitrile hydratase activity, said polypeptide having $\alpha^{(H)}$-subunit as defined in the Sequence Listing by SEQ ID: No. 1 and $\beta^{(H)}$-subunit as defined in the Sequence Listing by SEQ ID: No. 2.

2. A DNA comprising DNA$^{(H)}$ of claim 1 in a recombinant cloning vector.

3. Plasmid pNHJ10H obtained from E. coli TG1/pNHJ10H having Accession No. FERM BP-2777 containing the DNA according to claim 1.

4. A transformed cell containing the recombinant DNA of claim 2.

5. A method of producing nitrile hydratase which comprises culturing the transformant as claimed in claim 4 which is a prokaryote transformant and recovering nitrile hydratase from the culture.

6. A method of producing amides which comprises hydrating nitriles using nitrile hydratase obtained from the culture of the transformant of claim 4.

7. A method of producing amides which comprises culturing the transformant as claimed in claim 4, and hydrating nitriles to amides using the resultant culture, isolated bacterial cells, the supernatant of the culture, an extract of the culture, or a fixed material thereof.

8. An isolated DNA$^{(L)}$ fragment encoding a polypeptide having nitrile hydratase activity, said polypeptide having $\alpha^{(L)}$-subunit as defined in the Sequence Listing by SEQ ID: No. 3 and $\beta^{(L)}$-subunit as defined in the Sequence Listing by SEQ ID: No. 4.

9. A DNA comprising DNA$^{(L)}$ of claim 8 in a recombinant cloning vector.

10. Plasmid pNHJ20L obtained from E. coli TG1/pNHJ20L having Accession No. FERM BP-2778 containing the DNA according to claim 8.

11. A transformed cell containing the recombinant DNA of claim 9.

12. A method of producing nitrile hydratase which comprises culturing the transformant as claimed in claim 11 which is a prokaryote transformant and recovering nitrile hydratase from the culture.

13. A method of producing amides which comprises hydrating nitriles using nitrile hydratase obtained from the culture of the transformant of claim 11.

14. A method of producing amides which comprises culturing the transformant as claimed in claim 11, and hydrating nitriles to amides using the resultant culture, isolated bacterial cells, the supernatant of the culture, an extract of the culture, or a fixed material thereof.

* * * * *

UNITED STATES PATENT AND TRADEMARK OFFICE
CERTIFICATE OF CORRECTION

PATENT NO. : 5,753,472

DATED : May 19, 1998

INVENTOR(S) : Hideaki Yamada, Toru Nagasawa, Teruhiko Beppu, Sueharu Horinouchi and Makoto Nishiyama It is certified that error appears in the above-identified patent and that said Letters Patent is hereby corrected as shown below:

On the title page of the Patent, item [73], Assignee: add Teruhiko Beppu and Hideaki Yamada, both of Japan.

Signed and Sealed this

Fifteenth Day of December, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
    ( A ) LENGTH: 203 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
    ( A ) ORGANISM: Rhodococcus rhodochorus
    ( B ) STRAIN: J-1 (FERM BP-1478)

( x i ) SEQUENCE DESCRIPTION: SEQ ID NO:1:

```
Met  Ser  Glu  His  Val  Asn  Lys  Tyr  Thr  Glu  Tyr  Glu  Ala  Arg  Thr  Lys
 1              5                       10                          15

Ala  Ile  Glu  Thr  Leu  Leu  Tyr  Glu  Arg  Gly  Leu  Ile  Thr  Pro  Ala  Ala
            20                       25                      30

Val  Asp  Arg  Val  Val  Ser  Tyr  Tyr  Glu  Asn  Glu  Ile  Gly  Pro  Met  Gly
          35                      40                    45

Gly  Ala  Lys  Val  Val  Ala  Lys  Ser  Trp  Val  Asp  Pro  Glu  Tyr  Arg  Lys
       50                    55                 60

Trp  Leu  Glu  Glu  Asp  Ala  Thr  Ala  Ala  Met  Ala  Ser  Leu  Gly  Tyr  Ala
 65                         70                    75                          80

Gly  Glu  Gln  Ala  His  Gln  Ile  Ser  Ala  Val  Phe  Asn  Asp  Ser  Gln  Thr
```

|  |  |  | 85 |  |  |  |  | 90 |  |  |  |  | 95 |  |  |
|---|---|---|---|---|---|---|---|---|---|---|---|---|---|---|---|

His His Val Val Val Cys Thr Leu Cys Ser Cys Tyr Pro Trp Pro Val
                                 100                            105                      110

Leu Gly Leu Pro Pro Ala Trp Tyr Lys Ser Met Glu Tyr Arg Ser Arg
        115                          120                          125

Val Val Ala Asp Pro Arg Gly Val Leu Lys Arg Asp Phe Gly Phe Asp
        130                          135                       140

Ile Pro Asp Glu Val Glu Val Arg Val Trp Asp Ser Ser Ser Glu Ile
145                      150                          155                       160

Arg Tyr Ile Val Ile Pro Glu Arg Pro Ala Gly Thr Asp Gly Trp Ser
                     165                      170                       175

Glu Glu Glu Leu Thr Lys Leu Val Ser Arg Asp Ser Met Ile Gly Val
            180                      185                    190

Ser Asn Ala Leu Thr Pro Gln Glu Val Ile Val
        195                        200

( 2 ) INFORMATION FOR SEQ ID NO:2:

( i ) SEQUENCE CHARACTERISTICS:
        ( A ) LENGTH: 229 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Rhodococcus rhodochrous
        ( B ) STRAIN: J-1 (FERM BP-1478)

( x i ) SEQUENCE DESCRIPTION: SEQ ID NO:2:

Met Asp Gly Ile His Asp Thr Gly Gly Met Thr Gly Tyr Gly Pro Val
1                   5                      10                    15

Pro Tyr Gln Lys Asp Glu Pro Phe Phe His Tyr Glu Trp Glu Gly Arg
             20                      25                    30

Thr Leu Ser Ile Leu Thr Trp Met His Leu Lys Gly Ile Ser Trp Trp
        35                          40                    45

Asp Lys Ser Arg Phe Phe Arg Glu Ser Met Gly Asn Glu Asn Tyr Val
   50                        55                      60

Asn Glu Ile Arg Asn Ser Tyr Tyr Thr His Trp Leu Ser Ala Ala Glu
65                      70                          75                       80

Arg Ile Leu Val Ala Asp Lys Ile Ile Thr Glu Glu Glu Arg Lys His
                 85                          90                    95

Arg Val Gln Glu Ile Leu Glu Gly Arg Tyr Thr Asp Arg Lys Pro Ser
            100                      105                    110

Arg Lys Phe Asp Pro Ala Gln Ile Glu Lys Ala Ile Glu Arg Leu His
        115                        120                    125

Glu Pro His Ser Leu Ala Leu Pro Gly Ala Glu Pro Ser Phe Ser Leu
   130                        135                    140

Gly Asp Lys Ile Lys Val Lys Ser Met Asn Pro Leu Gly His Thr Arg
145                     150                        155                  160

Cys Pro Lys Tyr Val Arg Asn Lys Ile Gly Glu Ile Val Ala Tyr His
                 165                      170                    175

Gly Cys Gln Ile Tyr Pro Glu Ser Ser Ser Ala Gly Leu Gly Asp Asp
            180                      185                    190

Pro Arg Pro Leu Tyr Thr Val Ala Phe Ser Ala Gln Glu Leu Trp Gly
        195                        200                    205

Asp Asp Gly Asn Gly Lys Asp Val Val Cys Val Asp Leu Trp Glu Pro

-continued

```
              210                      215                      220

Tyr  Leu  Ile  Ser  Ala
    225
```

( 2 ) INFORMATION FOR SEQ ID NO:3:

( i ) SEQUENCE CHARACTERISTICS:
    ( A ) LENGTH: 207 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
    ( A ) ORGANISM: Rhodococcus rhodochrous
    ( B ) STRAIN: J-1 (FERM BP-1478)

( x i ) SEQUENCE DESCRIPTION: SEQ ID NO:3:

```
Met  Thr  Ala  His  Asn  Pro  Val  Gln  Gly  Thr  Leu  Pro  Arg  Ser  Asn  Glu
1                 5                        10                       15

Glu  Ile  Ala  Ala  Arg  Val  Lys  Ala  Met  Glu  Ala  Ile  Leu  Val  Asp  Lys
                20                        25                       30

Gly  Leu  Ile  Ser  Thr  Asp  Ala  Ile  Asp  His  Met  Ser  Ser  Val  Tyr  Glu
          35                        40                       45

Asn  Glu  Val  Gly  Pro  Gln  Leu  Gly  Ala  Lys  Ile  Val  Ala  Arg  Ala  Trp
     50                        55                       60

Val  Asp  Pro  Glu  Phe  Lys  Gln  Arg  Leu  Leu  Thr  Asp  Ala  Thr  Ser  Ala
65                       70                       75                       80

Cys  Arg  Glu  Met  Gly  Val  Gly  Gly  Met  Gln  Gly  Glu  Glu  Met  Val  Val
                    85                        90                       95

Leu  Glu  Asn  Thr  Gly  Thr  Val  His  Asn  Met  Val  Val  Cys  Thr  Leu  Cys
               100                       105                      110

Ser  Cys  Tyr  Pro  Trp  Pro  Val  Leu  Gly  Leu  Pro  Pro  Asn  Trp  Tyr  Lys
          115                       120                      125

Tyr  Pro  Ala  Tyr  Arg  Ala  Arg  Ala  Val  Arg  Asp  Pro  Arg  Gly  Val  Leu
     130                       135                      140

Ala  Glu  Phe  Gly  Tyr  Thr  Pro  Asp  Pro  Asp  Val  Glu  Ile  Arg  Ile  Trp
145                      150                       155                      160

Asp  Ser  Ser  Ala  Glu  Leu  Arg  Tyr  Trp  Val  Leu  Pro  Gln  Arg  Pro  Ala
                165                       170                      175

Gly  Thr  Glu  Asn  Phe  Thr  Glu  Glu  Gln  Leu  Ala  Asp  Leu  Val  Thr  Arg
               180                       185                      190

Asp  Ser  Leu  Ile  Gly  Val  Ser  Val  Pro  Thr  Thr  Pro  Ser  Lys  Ala
          195                       200                      205
```

( 2 ) INFORMATION FOR SEQ ID NO:4:

( i ) SEQUENCE CHARACTERISTICS:
    ( A ) LENGTH: 226 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
    ( A ) ORGANISM: Rhodococcus rhodochrous
    ( B ) STRAIN: J-1 (FERM BP-1478)

( x i ) SEQUENCE DESCRIPTION: SEQ ID NO:4:

```
Met  Asp  Gly  Ile  His  Asp  Leu  Gly  Gly  Arg  Ala  Gly  Leu  Gly  Pro  Ile
1                 5                        10                       15
```

| Lys | Pro | Glu | Ser<br>20 | Asp | Glu | Pro | Val<br>25 | Phe | His | Ser | Asp | Trp<br>30 | Glu | Arg | Ser |
|---|---|---|---|---|---|---|---|---|---|---|---|---|---|---|---|
| Val | Leu | Thr<br>35 | Met | Phe | Pro | Ala | Met<br>40 | Ala | Leu | Ala | Gly | Ala<br>45 | Phe | Asn | Leu |
| Asp | Gln<br>50 | Phe | Arg | Gly | Ala | Met<br>55 | Glu | Gln | Ile | Pro | Pro<br>60 | His | Asp | Tyr | Leu |
| Thr<br>65 | Ser | Gln | Tyr | Tyr | Glu<br>70 | His | Trp | Met | His | Ala<br>75 | Met | Ile | His | His | Gly<br>80 |
| Ile | Glu | Ala | Gly | Ile<br>85 | Phe | Asp | Ser | Asp | Glu<br>90 | Leu | Asp | Arg | Arg | Thr<br>95 | Gln |
| Tyr | Tyr | Met | Asp<br>100 | His | Pro | Asp | Asp | Thr<br>105 | Thr | Pro | Thr | Arg | Gln<br>110 | Asp | Pro |
| Gln | Leu | Val<br>115 | Glu | Thr | Ile | Ser | Gln<br>120 | Leu | Ile | Thr | His | Gly<br>125 | Ala | Asp | Tyr |
| Arg | Arg<br>130 | Pro | Thr | Asp | Thr | Glu<br>135 | Ala | Ala | Phe | Ala | Val<br>140 | Gly | Asp | Lys | Val |
| Ile<br>145 | Val | Arg | Ser | Asp | Ala<br>150 | Ser | Pro | Asn | Thr | His<br>155 | Thr | Arg | Arg | Ala | Gly<br>160 |
| Tyr | Val | Arg | Gly | Arg<br>165 | Val | Gly | Glu | Val | Val<br>170 | Ala | Thr | His | Gly | Ala<br>175 | Tyr |
| Val | Phe | Pro | Asp<br>180 | Thr | Asn | Ala | Leu | Gly<br>185 | Ala | Gly | Glu | Ser | Pro<br>190 | Glu | His |
| Leu | Tyr | Thr<br>195 | Val | Arg | Phe | Ser | Ala<br>200 | Thr | Glu | Leu | Trp | Gly<br>205 | Glu | Pro | Ala |
| Ala | Pro<br>210 | Asn | Val | Val | Asn | His<br>215 | Ile | Asp | Val | Phe | Glu<br>220 | Pro | Tyr | Leu | Leu |
| Pro<br>225 | Ala | | | | | | | | | | | | | | |

( 2 ) INFORMATION FOR SEQ ID NO:5:

( i ) SEQUENCE CHARACTERISTICS:
       ( A ) LENGTH: 609 base pairs
       ( B ) TYPE: nucleic acid
       ( C ) STRANDEDNESS: single
       ( D ) TOPOLOGY: linear ( i i ) MOLECULE TYPE: DNA (genomic)

( v i ) ORIGINAL SOURCE:
       ( A ) ORGANISM: Rhodococcus rhodochrous
       ( B ) STRAIN: J-1 (FERM BP-1478)

( x i ) SEQUENCE DESCRIPTION: SEQ ID NO:5:

```
GTGAGCGAGC ACGTCAATAA GTACACGGAG TACGAGGCAC GTACCAAGGC GATCGAAACC      60
TTGCTGTACG AGCGAGGGCT CATCACGCCC GCCGCGGTCG ACCGAGTCGT TTCGTACTAC     120
GAGAACGAGA TCGGCCCGAT GGGCGGTGCC AAGGTCGTGG CCAAGTCCTG GGTGGACCCT     180
GAGTACCGCA AGTGGCTCGA AGAGGACGCG ACGGCCGCGA TGGCGTCATT GGGCTATGCC     240
GGTGAGCAGG CACACCAAAT TCGGCGGTC TTCAACGACT CCCAAACGCA TCACGTGGTG      300
GTGTGCACTC TGTGTTCGTG CTATCCGTGG CCGGTGCTTG GTCTCCCGCC CGCCTGGTAC     360
AAGAGCATGG AGTACCGGTC CCGAGTGGTA GCGGACCCTC GTGGAGTGCT CAAGCGCGAT     420
TTCGGTTTCG ACATCCCCGA TGAGGTGGAG GTCAGGGTTT GGGACAGCAG CTCCGAAATC     480
CGCTACATCG TCATCCCGGA ACGGCCGGCC GGCACCGACG GTTGGTCCGA GGAGGAGCTG     540
ACGAAGCTGG TGAGCCGGGA CTCGATGATC GGTGTCAGTA ATGCGCTCAC ACCGCAGGAA     600
```

GTGATCGTA                                                                                     609

( 2 ) INFORMATION FOR SEQ ID NO:6:

( i ) SEQUENCE CHARACTERISTICS:
    ( A ) LENGTH: 687 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Rhodococcus rhodochrous
    ( B ) STRAIN: J-1 (FERM BP-1478)

( x i ) SEQUENCE DESCRIPTION: SEQ ID NO:6:

| | | | | | |
|---|---|---|---|---|---|
| ATGGATGGTA | TCCACGACAC | AGGCGGCATG | ACCGGATACG | GACCGGTCCC | CTATCAGAAG | 60
| GACGAGCCCT | TCTTCCACTA | CGAGTGGGAG | GGTCGGACCC | TGTCAATTCT | GACTTGGATG | 120
| CATCTCAAGG | GCATATCGTG | GTGGGACAAG | TCGCGGTTCT | TCCGGGAGTC | GATGGGAAC | 180
| GAAAACTACG | TCAACGAGAT | TCGCAACTCG | TACTACACCC | ACTGGCTGAG | TGCGGCAGAA | 240
| CGTATCCTCG | TCGCCGACAA | GATCATCACC | GAAGAAGAGC | GAAAGCACCG | TGTGCAAGAG | 300
| ATCCTTGAGG | GTCGGTACAC | GGACAGGAAG | CCGTCGCGGA | AGTTCGATCC | GGCCCAGATC | 360
| GAGAAGGCGA | TCGAACGGCT | TCACGAGCCC | CACTCCCTAG | CGCTTCCAGG | AGCGGAGCCG | 420
| AGTTTCTCTC | TCGGTGACAA | GATCAAAGTG | AAGAGTATGA | ACCGCTGGG | ACACACACGG | 480
| TGCCCGAAAT | ATGTGCGGAA | CAAGATCGGG | GAAATCGTCG | CCTACCACGG | CTGCCAGATC | 540
| TATCCCGAGA | GCAGCTCCGC | CGGCCTCGGC | GACGATCCTC | GCCCGCTCTA | CACGGTCGCG | 600
| TTTTCCGCCC | AGGAACTGTG | GGGCGACGAC | GGAAACGGGA | AAGACGTAGT | GTGCGTCGAT | 660
| CTCTGGGAAC | CGTACCTGAT | CTCTGCG | | | | 687

( 2 ) INFORMATION FOR SEQ ID NO:7:

( i ) SEQUENCE CHARACTERISTICS:
    ( A ) LENGTH: 621 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Rhodococcus rhodochrous
    ( B ) STRAIN: J-1 (FERM BP-1478)

( x i ) SEQUENCE DESCRIPTION: SEQ ID NO:7:

| | | | | | |
|---|---|---|---|---|---|
| ATGACCGCCC | ACAATCCCGT | CCAGGGCACG | TTGCCACGAT | CGAACGAGGA | GATCGCCGCA | 60
| CGCGTGAAGG | CCATGGAGGC | CATCCTCGTC | GACAAGGGCC | TGATCTCCAC | CGACGCCATC | 120
| GACCACATGT | CCTCGGTCTA | CGAGAACGAG | GTCGGTCCTC | AACTCGGCGC | CAAGATCGTC | 180
| GCCCGCGCCT | GGGTCGATCC | CGAGTTCAAG | CAGCGCCTGC | TCACCGACGC | CACCAGCGCC | 240
| TGCCGTGAAA | TGGGCGTCGG | CGGCATGCAG | GGCGAAGAAA | TGGTCGTGCT | GGAAAACACC | 300
| GGCACGGTCC | ACAACATGGT | CGTATGTACC | TTGTGCTCGT | GCTATCCGTG | GCCGGTTCTC | 360
| GGCCTGCCAC | CCAACTGGTA | CAAGTACCCC | GCCTACCGCG | CCCGCGCTGT | CCGCGACCCC | 420
| CGAGGTGTGC | TGGCCGAATT | CGGATATACC | CCCGACCCTG | ACGTCGAGAT | CCGGATATGG | 480
| GACTCGAGTG | CCGAACTTCG | CTACTGGGTC | CTGCCGCAAC | GCCCAGCCGG | CACCGAGAAC | 540
| TTCACCGAAG | AACAACTCGC | CGACCTCGTC | ACCCGCGACT | CGCTCATCGG | CGTATCCGTC | 600

CCCACCACAC CCAGCAAGGC C                                                                    621

( 2 ) INFORMATION FOR SEQ ID NO:8:

( i ) SEQUENCE CHARACTERISTICS:
        ( A ) LENGTH: 678 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Rhodococcus rhodochrous
        ( B ) STRAIN: J-1 (FERM BP-1478)

( x i ) SEQUENCE DESCRIPTION: SEQ ID NO:8:

ATGGATGGAA TCCACGACCT CGGTGGCCGC GCCGGCCTGG GTCCGATCAA GCCCGAATCC    60

GATGAACCTG TTTTCCATTC CGATTGGGAG CGGTCGGTTT TGACGATGTT CCCGGCGATG    120

GCGCTGGCCG GCGCGTTCAA TCTCGACCAG TTCCGGGGCG CGATGGAGCA GATCCCCCCG    180

CACGACTACC TGACCTCGCA ATACTACGAG CACTGGATGC ACGCGATGAT CCACCACGGC    240

ATCGAGGCGG GCATCTTCGA TTCCGACGAA CTCGACCGCC GCACCCAGTA CTACATGGAC    300

CATCCGGACG ACACGACCCC CACGCGGCAG GATCCGCAAC TGGTGGAGAC GATCTCGCAA    360

CTGATCACCC ACGGAGCCGA TTACCGACGC CCGACCGACA CCGAGGCCGC ATTCGCCGTA    420

GGCGACAAAG TCATCGTGCG GTCGGACGCC TCACCGAACA CCCACACCCG CCGCGCCGGA    480

TACGTCCGCG GTCGTGTCGG CGAAGTCGTG GCGACCCACG GCGCGTATGT CTTTCCGGAC    540

ACCAACGCAC TCGGCGCCGG CGAAAGCCCC GAACACCTGT ACACCGTGCG GTTCTCGGCG    600

ACCGAGTTGT GGGGTGAACC TGCCGCCCCG AACGTCGTCA ATCACATCGA CGTGTTCGAA    660

CCGTATCTGC TACCGGCC                                                  678

( 2 ) INFORMATION FOR SEQ ID NO:9:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Rhodococcus rhodochrous
        ( B ) STRAIN: J-1 (FERM BP-1478)

( x i ) SEQUENCE DESCRIPTION: SEQ ID NO:9:

Ser Glu His Val Asn Lys Tyr Thr Glu Tyr Glu Ala Arg Thr Lys Ala
1               5                   10                  15

Ile Glu Thr Leu Leu Tyr Glu Arg Gly Leu
            20              25

( 2 ) INFORMATION FOR SEQ ID NO:10:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Rhodococcus rhodochrous
        ( B ) STRAIN: J-1 (FERM BP-1478)

( x i ) SEQUENCE DESCRIPTION: SEQ ID NO:10:

Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu
            20              25

( 2 ) INFORMATION FOR SEQ ID NO:11:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( v i ) ORIGINAL SOURCE:
      ( A ) ORGANISM: Rhodococcus rhodochrous
      ( B ) STRAIN: J-1 (FERM BP-1478)

( x i ) SEQUENCE DESCRIPTION: SEQ ID NO:11:

Thr Ala His Asn Pro Val Gln Gly Thr Leu Pro Arg Xaa Asn Glu
1               5                   10                  15

( 2 ) INFORMATION FOR SEQ ID NO:12:

( i ) SEQUENCE CHARACTERISTICS:
      ( A ) LENGTH: 19 amino acids
      ( B ) TYPE: amino acid
      ( C ) STRANDEDNESS: single
      ( D ) TOPOLOGY: linear ( i i ) MOLECULE TYPE: peptide ( v i ) ORIGINAL SOURCE:
      ( A ) ORGANISM: Rhocococcus rhodochrous
      ( B ) STRAIN: J-1 (FERM BP-1478)

( x i ) SEQUENCE DESCRIPTION: SEQ ID NO:12:

Met Asp Gly Ile His Asp Leu Gly Gly Arg Ala Xaa Leu Xaa Pro Ile
1               5                   10                  15

Lys Pro Glu ( 2 ) INFORMATION FOR SEQ ID NO:13:

( i ) SEQUENCE CHARACTERISTICS:
      ( A ) LENGTH: 2070 base pairs
      ( B ) TYPE: nucleic acid
      ( C ) STRANDEDNESS: single
      ( D ) TOPOLOGY: linear ( i i ) MOLECULE TYPE: DNA (genomic)

( v i ) ORIGINAL SOURCE:
      ( A ) ORGANISM: Rhodococcus sp.
      ( B ) STRAIN: N-774 (FERM BP- 1936)

( i x ) FEATURE:
      ( A ) NAME/KEY: CDS
      ( B ) LOCATION: 675..1295

( i x ) FEATURE:
      ( A ) NAME/KEY: CDS
      ( B ) LOCATION: 1325..1960

( x i ) SEQUENCE DESCRIPTION: SEQ ID NO:13:

```
GCATGCTTTC CACATCTGGA ACGTGATCGC CACGGACGGT GGTGCCTACC AGATGTTGGA      60
CGGCAACGGA TACGGCATGA ACGCCGAAGG TTTGTACGAT CCGGAACTGA TGGCACACTT     120
```

```
TGCTTCTCGA CGCATTCAGC ACGCCGACGC TCTGTCCGAA ACCGTCAAAC TGGTGGCCCT        180

GACCGGCCAC CACGGCATCA CCACCCTCGG CGGCGCGAGC TACGGCAAAG CCCGGAACCT        240

CGTACCGCTT GCCCGCGCCG CCTACGACAC TGCCTTGAGA CAATTCGACG TCCTGGTGAT        300

GCCAACGCTG CCCTACGTCG CATCCGAATT GCCGGCGAAG GACGTAGATC GTGCAACCTT        360

CATCACCAAG GCTCTCGGGA TGATCGCCAA CACGGCACCA TTCGACGTGA CCGGACATCC        420

GTCCCTGTCC GTTCCGGCCG GCCTGGTGAA CGGGGTTCCG GTCGGAATGA TGATCACCGG        480

CAGACACTTC GACGATGCGA CAGTCCTTCG TGTCGGACGC GCATTCGAAA AGCTTCGCGG        540

CCGGTTTCCG ACGCCGGCCG AACGCGCCTC CAACTCTGCA CCACAACTCA GCCCCGCCTA        600

GTCCTGACGC ACTGTCAGAC AACAAATTCC ACCGATTCAC ACATGATCAG CCCACATAAG        660

AAAAGGTGAA CCAG ATG TCA GTA ACG ATC GAC CAC ACA ACG GAG AAC GCC         710
               Met Ser Val Thr Ile Asp His Thr Thr Glu Asn Ala
                1             5                      10

GCA CCG GCC CAG GCG GCG GTC TCC GAC CGG GCG TGG GCA CTG TTC CGC          758
Ala Pro Ala Gln Ala Ala Val Ser Asp Arg Ala Trp Ala Leu Phe Arg
        15              20                  25

GCA CTC GAC GGT AAG GGA TTG GTA CCC GAC GGT TAC GTC GAG GGA TGG          806
Ala Leu Asp Gly Lys Gly Leu Val Pro Asp Gly Tyr Val Glu Gly Trp
    30              35                  40

AAG AAG ACC TCC GAG GAG GAC TTC AGT CCA AGG CGC GGA GCG GAA TTG          854
Lys Lys Thr Ser Glu Glu Asp Phe Ser Pro Arg Arg Gly Ala Glu Leu
45              50                  55                  60

GTA GCG CGC GCA TGG ACC GAC CCC GAG TTC CGG CAG CTG CTT CTC ACC          902
Val Ala Arg Ala Trp Thr Asp Pro Glu Phe Arg Gln Leu Leu Leu Thr
                65              70                  75

GAC GGT ACC GCC GCA GTT GCC CAG TAC GGA TAC CTG GGC CCC CAG GCG          950
Asp Gly Thr Ala Ala Val Ala Gln Tyr Gly Tyr Leu Gly Pro Gln Ala
            80              85                  90

GCC TAC ATC GTG GCA GTC GAA GAC ACC CCG ACA CTC AAG AAC GTG ATC          998
Ala Tyr Ile Val Ala Val Glu Asp Thr Pro Thr Leu Lys Asn Val Ile
                95              100                 105

GTG TGC TCG CTG TGT TCA TGC ACC GCG TGG CCC ATC CTC GGT CTG CCA         1046
Val Cys Ser Leu Cys Ser Cys Thr Ala Trp Pro Ile Leu Gly Leu Pro
    110             115                 120

CCC ACC TGG TAC AAG AGC TTC GAA TAC CGT GCG CGC GTG GTC CGC GAA         1094
Pro Thr Trp Tyr Lys Ser Phe Glu Tyr Arg Ala Arg Val Val Arg Glu
125             130                 135                 140

CCA CGG AAG GTT CTC TCC GAG ATG GGA ACC GAG ATC GCG TCG GAC ATC         1142
Pro Arg Lys Val Leu Ser Glu Met Gly Thr Glu Ile Ala Ser Asp Ile
                145                 150                 155

GAG ATT CGC GTC TAC GAC ACC ACC GCC GAA ACT CGC TAC ATG GTC CTC         1190
Glu Ile Arg Val Tyr Asp Thr Thr Ala Glu Thr Arg Tyr Met Val Leu
            160                 165                 170

CCG CAG CGT CCC GCC GGC ACC GAA GGC TGG AGC CAG GAA CAA CTG CAG         1238
Pro Gln Arg Pro Ala Gly Thr Glu Gly Trp Ser Gln Glu Gln Leu Gln
        175                 180                 185

GAA ATC GTC ACC AAG GAC TGC CTG ATC GGG GTT GCA ATC CCG CAG GTT         1286
Glu Ile Val Thr Lys Asp Cys Leu Ile Gly Val Ala Ile Pro Gln Val
190                 195                 200

CCC ACC GTC TGATCACCCC GACAAGAAGG AAGCACACC ATG GAT GGA GTA CAC         1339
Pro Thr Val                                  Met Asp Gly Val His
205                                           1              5

GAT CTT GCC GGA GTA CAA GGC TTC GGC AAA GTC CCG CAT ACC GTC AAC         1387
Asp Leu Ala Gly Val Gln Gly Phe Gly Lys Val Pro His Thr Val Asn
            10              15                  20

GCC GAC ATC GGC CCC ACC TTT CAC GCC GAA TGG GAA CAC CTG CCC TAC         1435
Ala Asp Ile Gly Pro Thr Phe His Ala Glu Trp Glu His Leu Pro Tyr
```

|  |  |  |  |  |  |  |  |  |  |  |  |  |  |  |  |
|---|---|---|---|---|---|---|---|---|---|---|---|---|---|---|---|
| AGC | CTG | ATG | TTC | GCC | GGT | GTC | GCC | GAA | CTC | GGG | GCC | TTC | AGC | GTC | GAC | 1483 |
| Ser | Leu | Met 40 | Phe | Ala | Gly | Val | Ala 45 | Glu | Leu | Gly | Ala | Phe 50 | Ser | Val | Asp |
| GAA | GTG | CGA | TAC | GTC | GTC | GAG | CGG | ATG | GAG | CCG | GGC | CAC | TAC | ATG | ATG | 1531 |
| Glu | Val 55 | Arg | Tyr | Val | Val | Glu 60 | Arg | Met | Glu | Pro | Gly 65 | His | Tyr | Met | Met |
| ACC | CCG | TAC | TAC | GAG | AGG | TAC | GTC | ATC | GGT | GTC | GCG | ACA | TTG | ATG | GTC | 1579 |
| Thr 70 | Pro | Tyr | Tyr | Glu | Arg 75 | Tyr | Val | Ile | Gly | Val 80 | Ala | Thr | Leu | Met | Val 85 |
| GAA | AAG | GGA | ATC | CTG | ACG | CAG | GAC | GAA | CTC | GAA | AGC | CTT | GCG | GGG | GGA | 1627 |
| Glu | Lys | Gly | Ile | Leu 90 | Thr | Gln | Asp | Glu | Leu 95 | Glu | Ser | Leu | Ala | Gly 100 | Gly |
| CCG | TTC | CCA | CTG | TCA | CGG | CCC | AGC | GAA | TCC | GAA | GGG | CGG | CCG | GCA | CCC | 1675 |
| Pro | Phe | Pro | Leu 105 | Ser | Arg | Pro | Ser | Glu 110 | Ser | Glu | Gly | Arg | Pro 115 | Ala | Pro |
| GTC | GAG | ACG | ACC | ACC | TTC | GAA | GTC | GGG | CAG | CGA | GTA | CGC | GTA | CGC | GAC | 1723 |
| Val | Glu | Thr 120 | Thr | Thr | Phe | Glu | Val 125 | Gly | Gln | Arg | Val | Arg 130 | Val | Arg | Asp |
| GAG | TAC | GTT | CCG | GGG | CAT | ATT | CGA | ATG | CCT | GCA | TAC | TGC | CGT | GGA | CGA | 1771 |
| Glu | Tyr 135 | Val | Pro | Gly | His | Ile 140 | Arg | Met | Pro | Ala | Tyr 145 | Cys | Arg | Gly | Arg |
| GTG | GGA | ACC | ATC | TCT | CAT | CGA | ACT | ACC | GAG | AAG | TGG | CCG | TTT | CCC | GAC | 1819 |
| Val 150 | Gly | Thr | Ile | Ser | His 155 | Arg | Thr | Thr | Glu | Lys 160 | Trp | Pro | Phe | Pro | Asp 165 |
| GCA | ATC | GGC | CAC | GGG | CGC | AAC | GAC | GCC | GGC | GAA | GAA | CCG | ACG | TAC | CAC | 1867 |
| Ala | Ile | Gly | His | Gly 170 | Arg | Asn | Asp | Ala | Gly 175 | Glu | Glu | Pro | Thr | Tyr 180 | His |
| GTG | AAG | TTC | GCC | GCC | GAG | GAA | TTG | TTC | GGT | AGC | GAC | ACC | GAC | GGT | GGA | 1915 |
| Val | Lys | Phe | Ala 185 | Ala | Glu | Glu | Leu | Phe 190 | Gly | Ser | Asp | Thr | Asp 195 | Gly | Gly |
| AGC | GTC | GTT | GTC | GAC | CTC | TTC | GAG | GGT | TAC | CTC | GAG | CCT | GCG | GCC |  | 1960 |
| Ser | Val | Val 200 | Val | Asp | Leu | Phe | Glu 205 | Gly | Tyr | Leu | Glu | Pro 210 | Ala | Ala |  |

```
TGATCTTCCA GCATTCCAGG CGGCGGTCAC GCGATCACAG CGGTTCGTGC GACCGCCGCC    2020

TGATCACCAC GATTCACTCA TTCGGAAGGA CACTGGAAAT CATGGTCGAC              2070
```

( 2 ) INFORMATION FOR SEQ ID NO:14:

( i ) SEQUENCE CHARACTERISTICS:
        ( A ) LENGTH: 1970 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Rhodococcus rhodochrous
        ( B ) STRAIN: J-1 (FERM BP-1478)

( i x ) FEATURE:
        ( A ) NAME/KEY: CDS
        ( B ) LOCATION: 408..1094

( i x ) FEATURE:
        ( A ) NAME/KEY: CDS
        ( B ) LOCATION: 1111..1719

( x i ) SEQUENCE DESCRIPTION: SEQ ID NO:14:

```
CTGCAGCTCG AACATCGAAG GGTGCGAGCC GAGAGATCGG AGACGCAGAC ACCCGGAGGG    60

AACTTAGCCT CCCGGACCGA TGCGTGTCCT GGCAACGCCT CAAAATTCAG TGCAAGCGAT   120

TCAATCTTGT TACTTCCAGA ACCGAATCAC GTCCCCGTAG TGTGCGGGGA GAGCGCCCGA   180
```

```
ACGCAGGGAT GGTATCCATG CGCCCCTTCT CTTTTCGAAC GAGAACCGGC CGGTACAGCC       240

GACCCGGAGA CACTGTGACG CCGTTCAACG ATTGTTGTGC TGTGAAGGAT TCACCCAAGC       300

CAACTGATAT CGCCATTCCG TTGCCGGAAC ATTTGACACC TTCTCCCTAC GAGTAGAAGC       360

CAGCTGGACC CCTCTTTGAG CCCAGCTCCG ATGAAAGGAA TGAGGAA ATG GAT GGT         416
                                                    Met Asp Gly
                                                    1

ATC CAC GAC ACA GGC GGC ATG ACC GGA TAC GGA CCG GTC CCC TAT CAG         464
Ile His Asp Thr Gly Gly Met Thr Gly Tyr Gly Pro Val Pro Tyr Gln
    5              10                  15

AAG GAC GAG CCC TTC TTC CAC TAC GAG TGG GAG GGT CGG ACC CTG TCA         512
Lys Asp Glu Pro Phe Phe His Tyr Glu Trp Glu Gly Arg Thr Leu Ser
 20              25                  30                  35

ATT CTG ACT TGG ATG CAT CTC AAG GGC ATA TCG TGG TGG GAC AAG TCG         560
Ile Leu Thr Trp Met His Leu Lys Gly Ile Ser Trp Trp Asp Lys Ser
                40                  45                  50

CGG TTC TTC CGG GAG TCG ATG GGG AAC GAA AAC TAC GTC AAC GAG ATT         608
Arg Phe Phe Arg Glu Ser Met Gly Asn Glu Asn Tyr Val Asn Glu Ile
                55                  60                  65

CGC AAC TCG TAC TAC ACC CAC TGG CTG AGT GCG GCA GAA CGT ATC CTC         656
Arg Asn Ser Tyr Tyr Thr His Trp Leu Ser Ala Ala Glu Arg Ile Leu
            70                  75                  80

GTC GCC GAC AAG ATC ATC ACC GAA GAA GAG CGA AAG CAC CGT GTG CAA         704
Val Ala Asp Lys Ile Ile Thr Glu Glu Glu Arg Lys His Arg Val Gln
        85                  90                  95

GAG ATC CTT GAG GGT CGG TAC ACG GAC AGG AAG CCG TCG CGG AAG TTC         752
Glu Ile Leu Glu Gly Arg Tyr Thr Asp Arg Lys Pro Ser Arg Lys Phe
100                 105                 110                 115

GAT CCG GCC CAG ATC GAG AAG GCG ATC GAA CGG CTT CAC GAG CCC CAC         800
Asp Pro Ala Gln Ile Glu Lys Ala Ile Glu Arg Leu His Glu Pro His
                120                 125                 130

TCC CTA GCG CTT CCA GGA GCG GAG CCG AGT TTC TCT CTC GGT GAC AAG         848
Ser Leu Ala Leu Pro Gly Ala Glu Pro Ser Phe Ser Leu Gly Asp Lys
                135                 140                 145

ATC AAA GTG AAG AGT ATG AAC CCG CTG GGA CAC ACA CGG TGC CCG AAA         896
Ile Lys Val Lys Ser Met Asn Pro Leu Gly His Thr Arg Cys Pro Lys
            150                 155                 160

TAT GTG CGG AAC AAG ATC GGG GAA ATC GTC GCC TAC CAC GGC TGC CAG         944
Tyr Val Arg Asn Lys Ile Gly Glu Ile Val Ala Tyr His Gly Cys Gln
        165                 170                 175

ATC TAT CCC GAG AGC AGC TCC GCC GGC CTC GGC GAC GAT CCT CGC CCG         992
Ile Tyr Pro Glu Ser Ser Ser Ala Gly Leu Gly Asp Asp Pro Arg Pro
180                 185                 190                 195

CTC TAC ACG GTC GCG TTT TCC GCC CAG GAA CTG TGG GGC GAC GAC GGA        1040
Leu Tyr Thr Val Ala Phe Ser Ala Gln Glu Leu Trp Gly Asp Asp Gly
                200                 205                 210

AAC GGG AAA GAC GTA GTG TGC GTC GAT CTC TGG GAA CCG TAC CTG ATC        1088
Asn Gly Lys Asp Val Val Cys Val Asp Leu Trp Glu Pro Tyr Leu Ile
                215                 220                 225

TCT GCG TGAAAGGAAT ACGATA GTG AGC GAG CAC GTC AAT AAG TAC ACG          1137
Ser Ala              Met Ser Glu His Val Asn Lys Tyr Thr
                       1                   5

GAG TAC GAG GCA CGT ACC AAG GCG ATC GAA ACC TTG CTG TAC GAG CGA        1185
Glu Tyr Glu Ala Arg Thr Lys Ala Ile Glu Thr Leu Leu Tyr Glu Arg
 10                  15                  20                  25

GGG CTC ATC ACG CCC GCC GCG GTC GAC CGA GTC GTT TCG TAC TAC GAG        1233
Gly Leu Ile Thr Pro Ala Ala Val Asp Arg Val Val Ser Tyr Tyr Glu
                30                  35                  40

AAC GAG ATC GGC CCG ATG GGC GGT GCC AAG GTC GTG GCC AAG TCC TGG        1281
```

| | | | | | | | | | | | | | | | | |
|---|---|---|---|---|---|---|---|---|---|---|---|---|---|---|---|---|
| Asn | Glu | Ile | Gly<br>45 | Pro | Met | Gly | Gly | Ala<br>50 | Lys | Val | Val | Ala | Lys<br>55 | Ser | Trp | |
| GTG<br>Val | GAC<br>Asp | CCT<br>Pro<br>60 | GAG<br>Glu | TAC<br>Tyr | CGC<br>Arg | AAG<br>Lys | TGG<br>Trp<br>65 | CTC<br>Leu | GAA<br>Glu | GAG<br>Glu | GAC<br>Asp | GCG<br>Ala<br>70 | ACG<br>Thr | GCC<br>Ala | GCG<br>Ala | 1329 |
| ATG<br>Met | GCG<br>Ala<br>75 | TCA<br>Ser | TTG<br>Leu | GGC<br>Gly | TAT<br>Tyr | GCC<br>Ala<br>80 | GGT<br>Gly | GAG<br>Glu | CAG<br>Gln | GCA<br>Ala | CAC<br>His<br>85 | CAA<br>Gln | ATT<br>Ile | TCG<br>Ser | GCG<br>Ala | 1377 |
| GTC<br>Val<br>90 | TTC<br>Phe | AAC<br>Asn | GAC<br>Asp | TCC<br>Ser | CAA<br>Gln<br>95 | ACG<br>Thr | CAT<br>His | CAC<br>His | GTG<br>Val | GTG<br>Val<br>100 | GTG<br>Val | TGC<br>Cys | ACT<br>Thr | CTG<br>Leu | TGT<br>Cys<br>105 | 1425 |
| TCG<br>Ser | TGC<br>Cys | TAT<br>Tyr | CCG<br>Pro<br>110 | TGG<br>Trp | CCG<br>Pro | GTG<br>Val | CTT<br>Leu | GGT<br>Gly<br>115 | CTC<br>Leu | CCG<br>Pro | CCC<br>Pro | GCC<br>Ala | TGG<br>Trp<br>120 | TAC<br>Tyr | AAG<br>Lys | 1473 |
| AGC<br>Ser | ATG<br>Met | GAG<br>Glu<br>125 | TAC<br>Tyr | CGG<br>Arg | TCC<br>Ser | CGA<br>Arg | GTG<br>Val<br>130 | GTA<br>Val | GCG<br>Ala | GAC<br>Asp | CCT<br>Pro | CGT<br>Arg<br>135 | GGA<br>Gly | GTG<br>Val | CTC<br>Leu | 1521 |
| AAG<br>Lys | CGC<br>Arg | GAT<br>Asp<br>140 | TTC<br>Phe | GGT<br>Gly | TTC<br>Phe | GAC<br>Asp | ATC<br>Ile<br>145 | CCC<br>Pro | GAT<br>Asp | GAG<br>Glu | GTG<br>Val | GAG<br>Glu<br>150 | GTC<br>Val | AGG<br>Arg | GTT<br>Val | 1569 |
| TGG<br>Trp | GAC<br>Asp<br>155 | AGC<br>Ser | AGC<br>Ser | TCC<br>Ser | GAA<br>Glu | ATC<br>Ile<br>160 | CGC<br>Arg | TAC<br>Tyr | ATC<br>Ile | GTC<br>Val | ATC<br>Ile<br>165 | CCG<br>Pro | GAA<br>Glu | CGG<br>Arg | CCG<br>Pro | 1617 |
| GCC<br>Ala<br>170 | GGC<br>Gly | ACC<br>Thr | GAC<br>Asp | GGT<br>Gly | TGG<br>Trp<br>175 | TCC<br>Ser | GAG<br>Glu | GAG<br>Glu | GAG<br>Glu | CTG<br>Leu<br>180 | ACG<br>Thr | AAG<br>Lys | CTG<br>Leu | GTG<br>Val | AGC<br>Ser<br>185 | 1665 |
| CGG<br>Arg | GAC<br>Asp | TCG<br>Ser | ATG<br>Met | ATC<br>Ile<br>190 | GGT<br>Gly | GTC<br>Val | AGT<br>Ser | AAT<br>Asn | GCG<br>Ala<br>195 | CTC<br>Leu | ACA<br>Thr | CCG<br>Pro | CAG<br>Gln | GAA<br>Glu<br>200 | GTG<br>Val | 1713 |

```
ATC GTA TGAGTGAAGA CACACTCACT GATCGGCTCC CGGCGACTGG GACCGCCGCA      1769
Ile Val
CCGCCCCGCG ACAATGGCGA GCTTGTATTC ACCGAGCCTT GGGAAGCAAC GGCATTCGGG      1829

GTCGCCATCG CGCTTTCGGA TCAGAAGTCG TACGAATGGG AGTTCTTCCG ACAGCGTCTC      1889

ATTCACTCCA TCGCTGAGGC CAACGGTTGC GAGGCATACT ACGAGAGCTG ACAAAGGCG       1949

CTCGAGGCCA GCGTGGTCGA C                                                1970
```

( 2 ) INFORMATION FOR SEQ ID NO:15:

( i ) SEQUENCE CHARACTERISTICS:
        ( A ) LENGTH: 1731 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Rhodococcus rhodochrous
        ( B ) STRAIN: J-1 (FERM BP-1478)

( i x ) FEATURE:
        ( A ) NAME/KEY: CDS
        ( B ) LOCATION: 171..848

( i x ) FEATURE:
        ( A ) NAME/KEY: CDS
        ( B ) LOCATION: 915..1535

( x i ) SEQUENCE DESCRIPTION: SEQ ID NO:15:

```
GAGCTCCCTG GAGCCACTCG CGCCGACGCA TCCACGCTCG GACAGCCCAC GGTGCGGATC       60

ACCCCTGTTC GTCGGTAACA GAACAGTAAC ATGTCATCAG GTCATGACGT GTTGACGCAT      120

TAGACGAGGG CACATAGGGT TGGTGACTCA CGGCACAAGG AGAGCATTTC ATG GAT        176
                                                       Met Asp
```

```
                                                                                    1
GGA ATC CAC GAC CTC GGT GGC CGC GCC GGC CTG GGT CCG ATC AAG CCC                   224
Gly Ile His Asp Leu Gly Gly Arg Ala Gly Leu Gly Pro Ile Lys Pro
        5                  10                     15

GAA TCC GAT GAA CCT GTT TTC CAT TCC GAT TGG GAG CGG TCG GTT TTG                   272
Glu Ser Asp Glu Pro Val Phe His Ser Asp Trp Glu Arg Ser Val Leu
     20                     25                     30

ACG ATG TTC CCG GCG ATG GCG CTG GCC GGC GCG TTC AAT CTC GAC CAG                   320
Thr Met Phe Pro Ala Met Ala Leu Ala Gly Ala Phe Asn Leu Asp Gln
 35                     40                     45                     50

TTC CGG GGC GCG ATG GAG CAG ATC CCC CCG CAC GAC TAC CTG ACC TCG                   368
Phe Arg Gly Ala Met Glu Gln Ile Pro Pro His Asp Tyr Leu Thr Ser
                 55                     60                     65

CAA TAC TAC GAG CAC TGG ATG CAC GCG ATG ATC CAC CAC GGC ATC GAG                   416
Gln Tyr Tyr Glu His Trp Met His Ala Met Ile His His Gly Ile Glu
             70                     75                     80

GCG GGC ATC TTC GAT TCC GAC GAA CTC GAC CGC CGC ACC CAG TAC TAC                   464
Ala Gly Ile Phe Asp Ser Asp Glu Leu Asp Arg Arg Thr Gln Tyr Tyr
         85                     90                     95

ATG GAC CAT CCG GAC GAC ACG ACC CCC ACG CGG CAG GAT CCG CAA CTG                   512
Met Asp His Pro Asp Asp Thr Thr Pro Thr Arg Gln Asp Pro Gln Leu
    100                    105                    110

GTG GAG ACG ATC TCG CAA CTG ATC ACC CAC GGA GCC GAT TAC CGA CGC                   560
Val Glu Thr Ile Ser Gln Leu Ile Thr His Gly Ala Asp Tyr Arg Arg
115                    120                    125                    130

CCG ACC GAC ACC GAG GCC GCA TTC GCC GTA GGC GAC AAA GTC ATC GTG                   608
Pro Thr Asp Thr Glu Ala Ala Phe Ala Val Gly Asp Lys Val Ile Val
                135                    140                    145

CGG TCG GAC GCC TCA CCG AAC ACC CAC ACC CGC CGC GCC GGA TAC GTC                   656
Arg Ser Asp Ala Ser Pro Asn Thr His Thr Arg Arg Ala Gly Tyr Val
            150                    155                    160

CGC GGT CGT GTC GGC GAA GTC GTG GCG ACC CAC GGC GCG TAT GTC TTT                   704
Arg Gly Arg Val Gly Glu Val Val Ala Thr His Gly Ala Tyr Val Phe
        165                    170                    175

CCG GAC ACC AAC GCA CTC GGC GCC GGC GAA AGC CCC GAA CAC CTG TAC                   752
Pro Asp Thr Asn Ala Leu Gly Ala Gly Glu Ser Pro Glu His Leu Tyr
    180                    185                    190

ACC GTG CGG TTC TCG GCG ACC GAG TTG TGG GGT GAA CCT GCC GCC CCG                   800
Thr Val Arg Phe Ser Ala Thr Glu Leu Trp Gly Glu Pro Ala Ala Pro
195                    200                    205                    210

AAC GTC GTC AAT CAC ATC GAC GTG TTC GAA CCG TAT CTG CTA CCG GCC                   848
Asn Val Val Asn His Ile Asp Val Phe Glu Pro Tyr Leu Leu Pro Ala
                215                    220                    225

TGACCAGGTC ATCCGGTCCA CCCAGCGAGA CGTCCCTTCA CCACAGACAG AAACGAGCCC                 908

ACCCCG ATG ACC GCC CAC AAT CCC GTC CAG GGC ACG TTG CCA CGA TCG                    956
       Met Thr Ala His Asn Pro Val Gln Gly Thr Leu Pro Arg Ser
        1                   5                      10

AAC GAG GAG ATC GCC GCA CGC GTG AAG GCC ATG GAG GCC ATC CTC GTC                   1004
Asn Glu Glu Ile Ala Ala Arg Val Lys Ala Met Glu Ala Ile Leu Val
 15                     20                     25                     30

GAC AAG GGC CTG ATC TCC ACC GAC GCC ATC GAC CAC ATG TCC TCG GTC                   1052
Asp Lys Gly Leu Ile Ser Thr Asp Ala Ile Asp His Met Ser Ser Val
                 35                     40                     45

TAC GAG AAC GAG GTC GGT CCT CAA CTC GGC GCC AAG ATC GTC GCC CGC                   1100
Tyr Glu Asn Glu Val Gly Pro Gln Leu Gly Ala Lys Ile Val Ala Arg
             50                     55                     60

GCC TGG GTC GAT CCC GAG TTC AAG CAG CGC CTG CTC ACC GAC GCC ACC                   1148
Ala Trp Val Asp Pro Glu Phe Lys Gln Arg Leu Leu Thr Asp Ala Thr
         65                     70                     75
```

```
AGC GCC TGC CGT GAA ATG GGC GTC GGC GGC ATG CAG GGC GAA GAA ATG      1196
Ser Ala Cys Arg Glu Met Gly Val Gly Gly Met Gln Gly Glu Glu Met
     80              85                  90

GTC GTG CTG GAA AAC ACC GGC ACG GTC CAC AAC ATG GTC GTA TGT ACC      1244
Val Val Leu Glu Asn Thr Gly Thr Val His Asn Met Val Val Cys Thr
 95             100             105                         110

TTG TGC TCG TGC TAT CCG TGG CCG GTT CTC GGC CTG CCA CCC AAC TGG      1292
Leu Cys Ser Cys Tyr Pro Trp Pro Val Leu Gly Leu Pro Pro Asn Trp
             115             120                     125

TAC AAG TAC CCC GCC TAC CGC GCC CGC GCT GTC CGC GAC CCC CGA GGT      1340
Tyr Lys Tyr Pro Ala Tyr Arg Ala Arg Ala Val Arg Asp Pro Arg Gly
         130             135                     140

GTG CTG GCC GAA TTC GGA TAT ACC CCC GAC CCT GAC GTC GAG ATC CGG      1388
Val Leu Ala Glu Phe Gly Tyr Thr Pro Asp Pro Asp Val Glu Ile Arg
         145             150                 155

ATA TGG GAC TCG AGT GCC GAA CTT CGC TAC TGG GTC CTG CCG CAA CGC      1436
Ile Trp Asp Ser Ser Ala Glu Leu Arg Tyr Trp Val Leu Pro Gln Arg
     160             165                 170

CCA GCC GGC ACC GAG AAC TTC ACC GAA GAA CAA CTC GCC GAC CTC GTC      1484
Pro Ala Gly Thr Glu Asn Phe Thr Glu Glu Gln Leu Ala Asp Leu Val
175             180                 185                     190

ACC CGC GAC TCG CTC ATC GGC GTA TCC GTC CCC ACC ACA CCC AGC AAG      1532
Thr Arg Asp Ser Leu Ile Gly Val Ser Val Pro Thr Thr Pro Ser Lys
                 195             200                     205

GCC TGACATGCCC CGACTCAACG AACAACCCCA CCCGGGTCTC GAAGCCAACC           1585
Ala

TCGGCGACCT GGTACAGAAT CTGCCGTTCA ACGAACGAAT CCCCCGCCGC TCCGGCGAGG    1645

TCGCCTTCGA TCAGGCCTGG GAGATCCGCG CCTTCAGCAT TGCCACCGCA TTGCATGGCC    1705

AGGGCCGATT CGAATGGGAC GAATTC                                        1731
```